US012444528B2

(12) United States Patent
Sowards et al.

(10) Patent No.: US 12,444,528 B2
(45) Date of Patent: Oct. 14, 2025

(54) MAGNETIC SIGNATURE IMPRINTING SYSTEM

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 292 days.

(21) Appl. No.: 17/956,651

(22) Filed: Sep. 29, 2022

(65) Prior Publication Data

US 2023/0101371 A1 Mar. 30, 2023

Related U.S. Application Data

(60) Provisional application No. 63/250,734, filed on Sep. 30, 2021.

(51) Int. Cl.
*H01F 13/00* (2006.01)
*A61B 90/00* (2016.01)

(52) U.S. Cl.
CPC ............. *H01F 13/00* (2013.01); *A61B 90/39* (2016.02); *A61B 2090/3954* (2016.02)

(58) Field of Classification Search
CPC ..................... H01F 13/00; A61B 90/39; A61B 2090/3954
USPC .......................................................... 235/493
See application file for complete search history.

(56) References Cited

U.S. PATENT DOCUMENTS 4,940,966 A 7/1990 Pettigrew et al.
10,188,310 B2 1/2019 Derichs et al.
11,281,869 B2 3/2022 Vartiovaara
2002/0171547 A1* 11/2002 Johnston ................ G08B 13/06 340/568.1
2003/0094487 A1 5/2003 Blankenship et al.
(Continued)

FOREIGN PATENT DOCUMENTS

EP 2997901 A1 3/2016
WO 2013034175 A1 3/2013
(Continued)

OTHER PUBLICATIONS

PCT/US2022/044234 filed Sep. 21, 2022 International Search Report and Written Opinion dated Dec. 16, 2022.
(Continued)

*Primary Examiner* — Allyson N Trail
(74) *Attorney, Agent, or Firm* — Rutan & Tucker LLP

(57) ABSTRACT

Disclosed herein is a magnetic signature imprinting system including an imprinting device and a medical device having ferrous elements. The imprinting device includes an active area configured to receive the medical device. The active area includes one or more electromagnets configured to generate one or more electromagnetic fields to imprint a magnetic signature. The imprinting device further includes one or more sensors or a user input mechanism configured to detect one or more characteristics of the medical device and a console in communication with each of the electromagnets and the sensors.

20 Claims, 4 Drawing Sheets

(56) References Cited

U.S. PATENT DOCUMENTS

| | | | | |
|---|---|---|---|---|
| 2007/0114786 | A1* | 5/2007 | Antonenco | G06K 19/06187 283/70 |
| 2008/0041248 | A1* | 2/2008 | Kuwabara | G03F 7/0002 101/93.03 |
| 2009/0012418 | A1* | 1/2009 | Gerlach | A61B 5/412 600/550 |
| 2011/0148414 | A1* | 6/2011 | Teughels | B82Y 25/00 324/316 |
| 2013/0029112 | A1* | 1/2013 | Bargir | B42D 25/355 347/110 |
| 2014/0253270 | A1 | 9/2014 | Nicholls et al. | |
| 2014/0290512 | A1* | 10/2014 | Raksha | B41F 19/005 101/212 |
| 2015/0178522 | A1 | 6/2015 | Cato et al. | |
| 2016/0008091 | A1 | 1/2016 | Saotome et al. | |
| 2016/0262844 | A1 | 9/2016 | Cohen et al. | |
| 2017/0238996 | A1* | 8/2017 | Frame | A61B 34/20 |
| 2017/0347914 | A1 | 12/2017 | Isaacson et al. | |
| 2018/0117419 | A1* | 5/2018 | Jackson | A63B 71/0622 |
| 2018/0221610 | A1 | 8/2018 | Larson et al. | |
| 2018/0310955 | A1 | 11/2018 | Lindekugel et al. | |
| 2020/0250385 | A1* | 8/2020 | Narayanan | A61K 9/14 |
| 2020/0298493 | A1* | 9/2020 | Wilds | B33Y 50/00 |
| 2020/0360662 | A1 | 11/2020 | Ma et al. | |
| 2020/0405406 | A1* | 12/2020 | Harris | A61B 46/40 |
| 2021/0113113 | A1 | 4/2021 | Weprin et al. | |
| 2021/0174378 | A1* | 6/2021 | Rahimizad | G06Q 20/3672 |
| 2023/0096231 | A1* | 3/2023 | McLaughlin | H01F 13/00 600/424 |
| 2023/0102059 | A1* | 3/2023 | Sowards | A61B 5/055 324/309 |
| 2023/0285096 | A1* | 9/2023 | Lambrecht | A61B 34/35 |
| 2023/0334502 | A1* | 10/2023 | Top | G06Q 20/3825 |
| 2025/0182946 | A1 | 6/2025 | McLaughlin et al. | |

FOREIGN PATENT DOCUMENTS

| | | | |
|---|---|---|---|
| WO | 2023055628 | A1 | 4/2023 |
| WO | 2023055821 | A1 | 4/2023 |
| WO | 2023055958 | A1 | 4/2023 |

OTHER PUBLICATIONS

PCT/US2022/045069 filed Sep. 28, 2022 International Search Report and Written Opinion dated Mar. 14, 2023.

PCT/US2022/045264 filed Sep. 29, 2022 International Search Report and Written Opinion dated Jan. 27, 2023.

PCT/US2022/044234 filed Sep. 21, 2022 International Preliminary Report on Patentability dated Apr. 2, 2024.

U.S. Appl. No. 17/949,679, filed Sep. 21, 2022 Non-Final Office Action dated May 22, 2024.

U.S. Appl. No. 17/949,679, filed Sep. 21, 2022 Non-Final Office Action dated Oct. 25, 2024.

U.S. Appl. No. 17/955,120, filed Sep. 28, 2022 Notice of Allowance dated Sep. 25, 2024.

U.S. Appl. No. 17/949,679, filed Sep. 21, 2022 Advisory Action dated Jun. 5, 2025.

U.S. Appl. No. 17/949,679, filed Sep. 21, 2022 Non-Final Office Action dated Jul. 8, 2025.

* cited by examiner

MAGNETIC SIGNATURE IMPRINTING SYSTEM

PRIORITY

This application claims the benefit of priority to U.S. Provisional Application No. 63/250,734, filed Sep. 30, 2021, which is incorporated by reference in its entirety into this application.

BACKGROUND

Medical devices may include a magnetic signature that may be tracked in three-dimensional space. Current methodologies are limited to producing a single magnetic signature. Furthermore, tracking systems are limited in their compatibility. It would be beneficial to the user to have a magnetic signature imprinting system that generates customizable magnetic signatures to all types, shapes and sizes of medical device. Disclosed here is a magnetic signature imprinting system and method of use that address the foregoing.

SUMMARY

Disclosed herein is a magnetic signature imprinting system that, according to some embodiments, includes an imprinting apparatus configured to operatively engage a medical device. The imprinting apparatus includes a frame; a device engagement mechanism coupled with the frame, where the device engagement mechanism is configured to receive and position the medical device within an imprinting space of the frame; and a number of electromagnets disposed within the imprinting space. The system further includes a console coupled with the one or more electromagnets, the console having a number of processors and a non-transitory computer-readable medium having logic stored thereon that, when executed by the processors, performs operations that include selectively activating one or more of the number to electromagnets to imprint a defined magnetic signature on the medical device to define an imprinted magnetic signature. In some embodiments, the medical device includes a needle, a stylet, a guidewire, an obturator, a probe, or a tunneller.

In some embodiments, the magnetic signature includes a series of dipoles disposed along the medical device. In some embodiments, at least one dipole includes a first length and at least one other dipole includes a second length different from the first length. In some embodiments, at least one dipole includes a first orientation and at least one other dipole includes a second orientation rotated 180 degrees from the first orientation. In some embodiments, a first spacing between a first pair of adjacent dipoles is different from a second spacing between a second pair of adjacent dipoles. In some embodiments, the magnetic signature includes one or more multipoles disposed along the medical device.

In some embodiments, the system further includes a number of identification sensors coupled with the console, where the number of identification sensors are configured to provide at least one of data or electrical signals associated with one or more characteristics of the medical device, and where the operations further include (i) receiving the at least one of data or electrical signals from the number of identification sensors, (ii) determining an identity of the medical device based on the at least one of data or electrical signals, and (iii) establishing the defined magnetic signature based on the identity.

In some embodiments, the number of identification sensors includes a radio frequency identification (RFID) reader, and the operations further include receiving RFID data from an RFID tag associated with the medical device, where the RFID data includes the identity. Similarly, in some embodiments, the number of identification sensors includes a barcode reader, and the operations further include obtaining barcode data from a barcode associated with the medical device, where the barcode data includes the identity.

In some embodiments, the number of identification sensors includes one or more first sensors configured to provide the at least one of data or electrical signals based on a number of physical characteristics of the medical device, and the operations further include determining the identity based on the number of physical characteristics. In some embodiments, the number of physical characteristics include one or more of a physical dimension or a shape of the medical device. In some embodiments, the physical dimension includes at least one of a length or a diameter of the medical device. In some embodiments, one or more first sensors include at least one of an inductive sensor, an impedance sensor, a capacitive sensor, or an optical sensor.

In some embodiments, the system further a number of magnetometers coupled with the console, where the magnetometers are configured to detect a magnetic field generated by the imprinted magnetic signature on the medical device, and the operations further include (i) receiving electrical signals from the magnetometers based on the magnetic field generated by the imprinted magnetic signature, (ii) determining the imprinted magnetic signature on the medical device from the electrical signals from the magnetometers, (iii) comparing the imprinted magnetic signature with the defined magnetic signature to verify that the imprinted magnetic signature matches the defined magnetic signature, and (iv) providing an alert to the operator in response to the comparison.

In some embodiments, activating one or more of the electromagnets includes activating a pair of electromagnets that are separated by an electromagnet spacing, where the electromagnet spacing defines a spacing between adjacent dipoles of the magnetic signature.

In some embodiments, activating one or more of the electromagnets includes (i) activating a first pair of electromagnets separated by a first electromagnet spacing, where the first electromagnet spacing defines a first spacing be adjacent dipoles; and (ii) activating a second pair of electromagnets separated by a second electromagnet spacing, where the second electromagnet spacing defines a second spacing be adjacent dipoles, and where second spacing be adjacent dipoles is different from the first spacing be adjacent dipoles.

In some embodiments, the number of electromagnets includes a first electromagnet having a first electromagnet length and second electromagnet having a second electromagnet length different from the first electromagnet length, and activating one or more of the electromagnets includes (i) activating the first electromagnet to imprint a dipole having a first dipole length and (ii) activating the second electromagnet to imprint a dipole having a second dipole length, where the second dipole length is different from the first dipole length.

In some embodiments, the console includes a power converted configured to supply power to the electromagnets in a first polarity and an opposite second polarity, and activating one or more of the number of electromagnets includes (i) supplying power to one electromagnet in a first polarity to imprint a first dipole having a first orientation, and (ii) supplying power to the one electromagnet in a second polarity to imprint a second dipole having a second orientation opposite the first orientation.

In some embodiments, the device engagement mechanism is configured to displace the medical device along the imprinting space, and activating one or more of the number of electromagnets includes (i) activating a first subset of the electromagnets, (ii) displacing the medical device from a first position within the imprinting space to a second position within the imprinting space, and (iii) activating a second subset of the electromagnets.

In some embodiments, the imprinting apparatus includes a number of position sensors configured to determine a longitudinal position of the medical device within the imprinting space, and the operations further include at least one of (i) notifying the operator regarding the longitudinal position of the medical device or (ii) adjusting the position of the medical device via the device engagement mechanism.

In some embodiments, the number of position sensors includes one more magnetometers configured to determine a longitudinal position of at least a portion of the imprinted magnetic signature within the imprinting space, and the operations further include adjusting the position of the medical device via the device engagement mechanism to move the at least a portion of the imprinted magnetic signature from a first position within the imprinting space to a second position within the imprinting space.

Also disclosed herein is a method of imprinting a magnetic signature onto a medical device that, according to some embodiments, includes (i) receiving at least a portion of the medical device within an imprinting space of a magnetic signature imprinting system, (ii) determining an identity of the medical device, (iii) determining a defined magnetic signature to imprint onto the medical device, (iv) imprinting a magnetic signature based on the defined magnetic signature onto the medical device to define an imprinted magnetic signature, and (v) validating that the imprinted magnetic signature matches the defined magnetic signature.

In some embodiments of the method, the magnetic signature includes a series of dipoles disposed along the medical device.

In some embodiments, the method further includes receiving at least one of data or electrical signals from a number of sensors of the system, where the at least one of data or electrical signals is based on a number of physical characteristics of the medical device, and where determining an identity of the medical device is based on at least one of the number of physical characteristics of the medical device.

In some embodiments of the method, validating the imprinted magnetic signature includes (i) determining the imprinted magnetic signature via a number of magnetometers of the system, and (ii) comparing the imprinted magnetic signature with the defined magnetic signature to verify that the imprinted magnetic signature matches the defined magnetic signature.

In some embodiments of the method, the magnetic signature includes a number of dipoles disposed along the medical device, and imprinting a magnetic signature includes activating one or more electromagnets of the system, where each electromagnet is configured to imprint a dipole onto the medical device when activated.

In some embodiments of the method, activating one or more electromagnets includes (i) activating a first pair of electromagnets separated by a first electromagnet spacing, where the first electromagnet spacing defines a first spacing be adjacent dipoles; and (ii) activating a second pair of electromagnets separated by a second electromagnet spacing, where the second electromagnet spacing defining a second spacing be adjacent dipoles, and where second spacing between adjacent dipoles is different from the first spacing between adjacent dipoles.

In some embodiments of the method, the number of electromagnets includes a first electromagnet having a first electromagnet length and second electromagnet having a second electromagnet length different from the first electromagnet length, and activating one or more electromagnets includes activating the first electromagnet to imprint a dipole having a first dipole length and activating the second electromagnet to imprint a dipole having a second dipole length, wherein the second dipole length is different from the first dipole length.

In some embodiments of the method, a power converted of the system is configured to supply power to the electromagnets in a first polarity and an opposite second polarity, and activating one or more of the number of electromagnets includes (i) supplying power to one electromagnet in a first polarity to imprint a first dipole having a first orientation, and (ii) supplying power to the one electromagnet in a second polarity to imprint a second dipole having a second orientation opposite the first orientation.

In some embodiments of the method, a device engagement mechanism of the system is configured to displace the medical device along the imprinting space, and activating one or more of the number of electromagnets includes (i) activating a first subset of the electromagnets, (ii) displacing the medical device from a first position within the imprinting space to a second position within the imprinting space, and (iii) activating a second subset of the electromagnets.

In some embodiments of the method, imprinting a magnetic signature includes (i) determining a longitudinal position of at least a portion of the imprinted magnetic signature within the imprinting space via one or more magnetometers of the system, and (ii) displacing the medical device via device engagement mechanism to adjust the longitudinal position of the at least a portion of the imprinted magnetic signature within the imprinting space.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
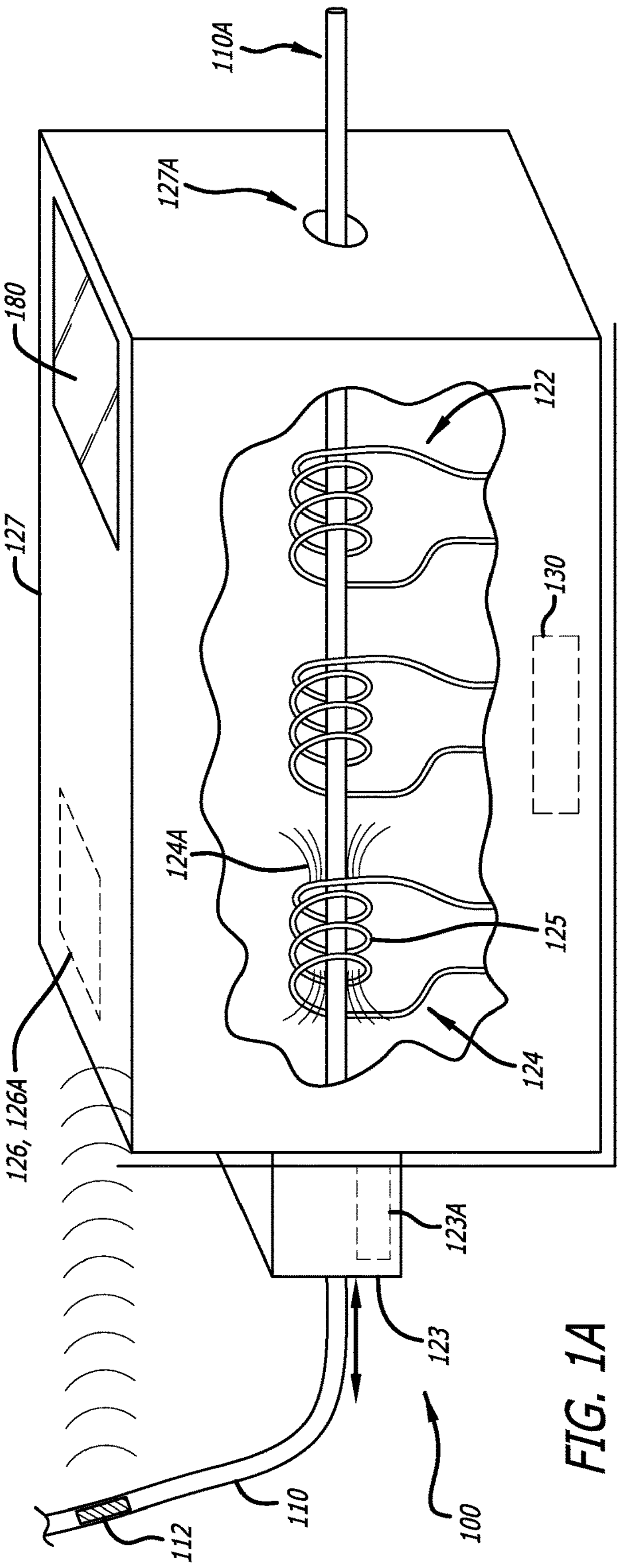
FIG. 1A illustrates a perspective view of a magnetic signature imprinting system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

Unless defined otherwise, all technical and scientific terms used herein have the same meaning as commonly understood by those of ordinary skill in the art.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Figure 1B:
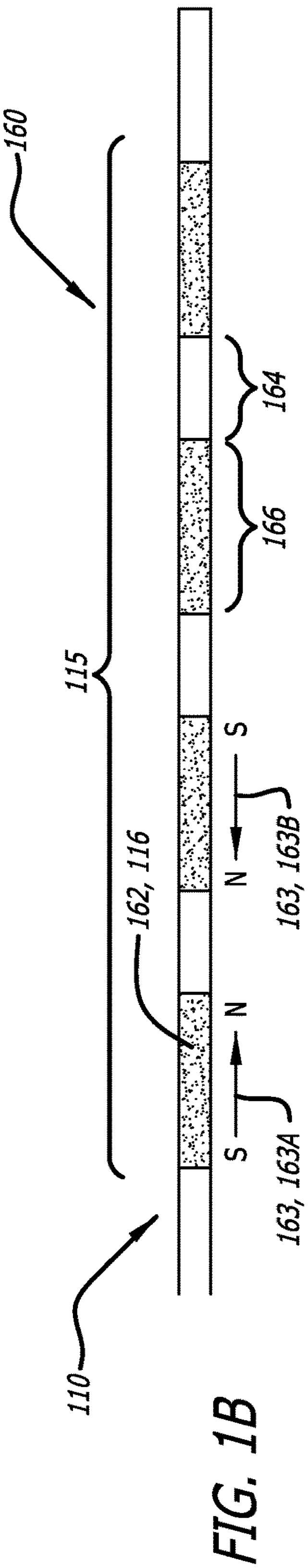
FIG. 1B illustrates a side view of a medical device having a magnetic signature imprinted there by the system of FIG. 1A, in accordance with some embodiments.

FIG. 1A illustrates a perspective view of a magnetic signature imprinting system 100, in accordance with some embodiments. The magnetic signature imprinting system ("system") 100 may include an imprinting device or apparatus 120 that is generally configured to imprint a magnetic signature onto a medical device 110. The system 100 may also include a user interface 180. The imprinting device 120 includes a body or frame 127 having an opening 127A extending through the body 127. The imprinting device 120 includes an active area 122 (i.e., an imprinting space), where the active area 122 is configured to receive the medical device 110 therein via the opening 127A. The magnetic signature is imprinted onto the medical device 110 within the active area 122. The imprinting device 120 includes a number (e.g., 1, 2, 3, 4, or more) electromagnets 124 disposed within the active area 122, where the electromagnets 124, when activated, are configured to imprint the magnetic signature onto the medical device 110 as further described below. Throughout this disclosure, a "defined magnetic signature" shall mean the magnetic signature intended to be imprinted onto the medical device 110. Similarly, an "imprinted magnetic signature" shall mean the magnetic signature that has been imprinted on the medical device FIG. 1B illustrates a side view of the medical device 110 having the magnetic signature 160 imprinted onto a signature portion 115 of the medical device 110. The medical device 110 may include a needle, a stylet, guidewire, an obturator, a probe, a tunneller, a stent, a port, a balloon device, a sheath, or any other medical device without limit. The signature portion 115 may generally be configured to receive the magnetic signature 160. For example, the signature portion 115 may include ferrous elements 116, where the ferrous elements 116 are portions or segments of the medical device 110 that are magnetizable, i.e., capable of being magnetized. In some embodiments, the signature portion 115 may a number (e.g., 1, 5, 20, or 100) of discreet ferrous elements 116.

The magnetic signature 150 includes a number (1, 2, 3, 4, 5, 6, or more) of magnetic dipoles (dipoles) 162 disposed along the signature portion 115. In some embodiments, the dipoles 162 may be imprinted onto the ferrous elements 116 in a one-to-one relationship. In some embodiments, one dipole 162 may include (i.e., extend across) more than one ferrous element 116. In some embodiments, one or more one ferrous elements 116 may not include a dipole 162 imprinted thereon.

Each dipole 162 defines an orientation 163 in accordance with the North and South poles of the dipole 162. As such, the orientation of each dipole 162 may be a first orientation 163A or a second orientation 163B, where the second orientation 163B is rotated 180 degrees from the first orientation 162A. Each dipole 162 may also define a length 166. In some embodiments, the length 166 may be chosen from a number (e.g., 1, 2, 3, 4, 5, 6, or more) of discrete lengths. For example, a first dipole 132 may define a first length and a second dipole may define a second length, where the second length is different from the first length. Similarly, the magnetic signature 150 may include a spacing 164 between adjacent dipoles 132. In some embodiments, the spacing 164 may be chosen from a number (e.g., 1, 2, 3, 4, 5, 6, or more) of discrete spacings. For example, a first pair of adjacent dipoles 132 may define a first spacing and a second pair of adjacent dipoles 132 may define a second spacing, where the second spacing is different from the first spacing. In some embodiments, the dipoles 162 may include magnetized discreet ferrous elements 116. The magnetic signature 160 may include any combination of all or any subset of the number of dipoles 162, the spacing 164 between adjacent dipoles 162, the orientation 163 of each of the dipoles 162, and the length 166 of each of the dipoles 162. In some embodiments, the magnetic signature 160 may include one or more magnetic multipoles.

Referring to both FIGS. 1A and 1B, each electromagnet 124 is configured to imprint a dipole 162 onto the medical device 110. Each electromagnet 124 includes a coil 125 configured to define a magnetic field 124A when the coil 125 is energized. Each electromagnet 124 is positioned and oriented within the active area 122 so that the medical device 110 extends through the coil 125, such as along a central axis of the coil 125. As such, the dipole 162 imprinted onto the medical device 110 is oriented parallel to a longitudinal axis of the medical device 110, i.e., extends along the medical device 110.

The coil 125 of each electromagnet 124 extends along the active area an electromagnet length. In some embodiments, the electromagnet length defines the length 166 of the dipole 162 imprinted on the medical device 110 by the respective electromagnet 125. In some embodiments, a first electromagnet 124 may define a first electromagnet length a second electromagnet 124 may define a second electromagnet length, where the second electromagnet length is different from the first electromagnet length.

Similarly, pair of electromagnets 124 may define an electromagnet spacing between the corresponding electromagnets 124. In some embodiments, the electromagnet spacing may define the spacing 164 between adjacent dipoles 162 of the magnetic signature 160. In some embodiments, a pair of electromagnets 124 may define a first electromagnet spacing and a second pair of electromagnets 124 may define a second electromagnet spacing, where the second electromagnet spacing is different from the first electromagnet spacing.

In some embodiments, the imprinting device 120 may include other electromagnets that include an orientation other than parallel to the medical device 110. Such other electromagnets may be configured to imprint a dipole onto the medical device 110 having an orientation other than parallel to the medical device 110, such as perpendicular to the medical device 110, for example. Further, the imprinting device 120 may include a series of other electromagnets configured to imprint multiple dipoles defining multiple orientations, that when combined form a multipole.

In some embodiments, the device 120 may include one or more sensors 126 in communication with the console 140. The one or more sensors 126 in combination with the console 140 may generally be configured to identify (i.e., determine an identity) of the medical device 110. In some embodiments, the one or more sensors 126 be configured to detect one or more characteristics (e.g., physical characteristics) of the medical device 110, such as the size of the medical device 110, the shape of the medical device 110, or the location of the ferrous elements 116 on the medical device 110, for example. In some embodiments, the one or more characteristics may include a length and/or a diameter of a medical device 110. In some embodiments, the system 100 may determine the identity of the medical device 110 and define the magnetic signature 160 (i.e., established a defined magnetic signature) to be imprinted on the medical device 110 based on the identity. In some embodiments, the one or more sensors 126 may include any sensor suitable for determining a physical characteristic of the medical device, such as an impedance sensor, an optical sensor, a capacitive sensor, a proximity sensor, or a magnetometer, for example. The one or more sensors 126 may be configured to provide data or electrical signals to the console 140.

In some embodiments, the one or more sensors 126 may be configured to determine a longitudinal position of the medical device 110 within the active area 122. For example, the one or more sensors 126 may be configured to detect a first end 110A of the medical device 110 and thereby determine or track the position of the medical device 110.

In some embodiments, the one or more sensors 126 may include an RFID reader 126A and the medical device 110 may include an RFID tag 112, where the data acquired from the RFID tag 112 includes the identity of the medical device 110. In some embodiments, the one or more sensors 126 may include a barcode reader, and the medical device 110 may associated with a barcode where the barcode data includes the identity.

In some embodiments, the one or more sensors 126 may include one or more magnetometers, where the one or more magnetometers in combination with console 140 are configured to detect the magnetic signature 160, i.e., read or otherwise determine the imprinted magnetic signature 160 on the medical device 110. In some embodiments, the magnetometers may be configured to determine a position of the magnetic signature 160 along the active area 122.

The device 120 may include a device engagement mechanism 123 configured to displace or longitudinally position the medical device 110 within or along the active area 122. The device engagement mechanism 123 is operatively coupled with an engagement actuator 123A, and the engagement actuator 123A is coupled with the console 130 so that logic of the console 130 may govern the operation of the engagement actuator 123A and thereby, govern the position of the medical device 110 along the active area 122 with respect to the electromagnets 124. In some embodiments of operation, the system 100 may (i) activate a first subset of the electromagnets 124, (ii) displace the medical device 110 from a first position within the active area 122 to a second position within the active area 122 via the device engagement mechanism 123, and (iii) activate a second subset of the electromagnets 124.

The electromagnets 124 are coupled with the console 130 so that logic of the console 130 may govern the operation of each electromagnet 124 individually, where operation of the electromagnet 124 includes activating and deactivating the electromagnets 124, i.e., energizing and de-energizing the corresponding coil 125. The operation of the electromagnet 124 may further include defining a polarity of the electromagnet 124, i.e., the direction of current though the corresponding coil 125, where the polarity of the electromagnet 124 defines the orientation of the dipole 162 imprinted onto the medical device 110.

Figure 2:
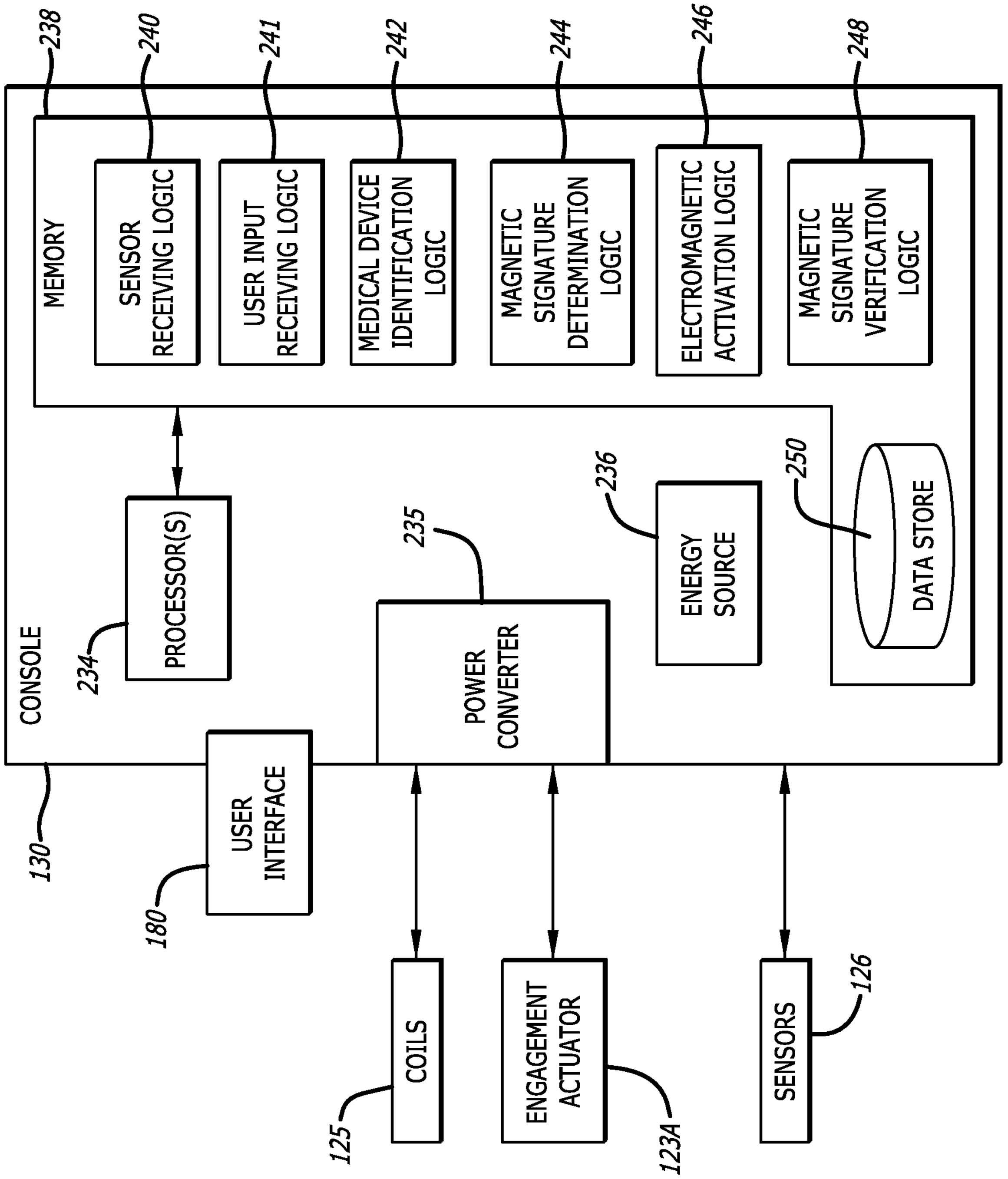
FIG. 2 illustrates a block diagram of the console of the system of FIG. 1A, in accordance with some embodiments.

FIG. 2 illustrates a block diagram of the system 100 including the console 130, in accordance with some embodiments. In some embodiments, the console 130 may include one or more processors 234, an energy source 236, non-transitory computer readable medium ("memory") 238, and a plurality of logic modules. In some embodiments, the energy source 236 may be configured provide power to the console 130 generally including a power converter 235. The power converter 235 may be configured to provide power to the one or more sensors 126, the engagement actuator 123A, and the coils 132. In some embodiments, the energy source 236 may include a rechargeable battery or an external power source. In some embodiments, the plurality of logic modules may include one or more of a sensor receiving logic 240, a user input mechanism receiving logic 241, a medical device identification logic 242, a magnetic signature determination logic 244, an electromagnetic activation logic 246, a magnetic signature verification logic 248, and a data store 250. In some embodiments, the sensor receiving logic 240 may be configured to receive one or more sensor values from the one or more sensors 126. In some embodiments, the one or more sensor values (e.g., data or electric signals) may correspond to the one or more characteristics. In an embodiment, wherein the sensor 126 is a RFID reader or a barcode scanner, the sensor receiving logic 240 may be configured to receive the values contained within a RFID tag or the barcode (e.g., serial number of the medical device). In some embodiments, the user input receiving logic 241 may be configured to receive one or more user values from the user interface 180, the one or more user values corresponding to the one or more characteristics or the identity of the medical device 110, generally. In some embodiments, the medical device identification logic 242 may be configured to determine the identity of the medical device 110. In some embodiments, the medical device identification logic 242 may be configured to determine the identity of the medical device 110 using the one or more sensor values or the one or more user values. Determining the identity of the medical device 110 may also include determining the location of the ferrous elements 116 along the medical device 110, the size of the medical device 110, and/or the shape of the medical device 110. In some embodiments, determining the identity of the medical device 110 may be utilized to define the magnetic signature 160 to be imprinted thereon and thereby define the operation of the electromagnets 124 and the device engagement mechanism 123 consistent with imprinting the defined magnetic signature 160.

In some embodiments, the magnetic signature determination logic 244 may be configured to define the magnetic signature to be imprinted onto the medical device 110 and the operation of the one or more electromagnets 124 within the active area 122 needed to imprint the magnetic signature. In some embodiments, the magnetic signature determination logic 244 may be configured to use the identity of the medical device 110 to define the magnetic signature 160. In some embodiments, the magnetic signature determination logic 244 may be configured to use the one or more characteristics of the medical device 110, as determined by the one or more sensors 126, to determine the magnetic signature 160. In some embodiments, the medical device 110 may be moved through the active area 122 and the magnetic signature 160 may be imprinted onto the medical device 110. In some embodiments, the electromagnetic activation logic 246 may be configured to activate and deactivate the electromagnets 124 to generate the one or more electromagnetic fields necessary to imprint the determined magnetic signature 160 on the medical device 110. Since the magnetic signature 160 may be imprinted on the medical device 110 as the medical device 110 moves through the active area 122, the electromagnetic activation logic 246 may activate each of the electromagnets 124 independently to imprint a portion of the magnetic signature 160 on the medical device 110. The movement of the medical device 110 through the active area 122 combined with the activation and deactivation of the electromagnets 124 may be used to imprint the magnetic signature 160 onto the medical device 110.

In some embodiments, the magnetic signature verification logic 248 may be configured to verify that the imprinted magnetic signature 160 matches the defined magnetic signature 160. In some embodiments, the one or more sensors 126 may include one or more magnetometers configured to detect the magnetic signature 160 and the magnetic signature verification logic 248 may compare the imprinted magnetic signature 160 with the defined magnetic signature 160. In some embodiments, the magnetic signature verification logic 248 may provide an alert to the operator in response to the comparison. In some embodiments, the data store 250 may be configured to store one or more templates of the defined magnetic signature 160 for any or all of the medical devices 110 that may be detected by the one or more sensors 126 and identified by the logic.

Figure 3:
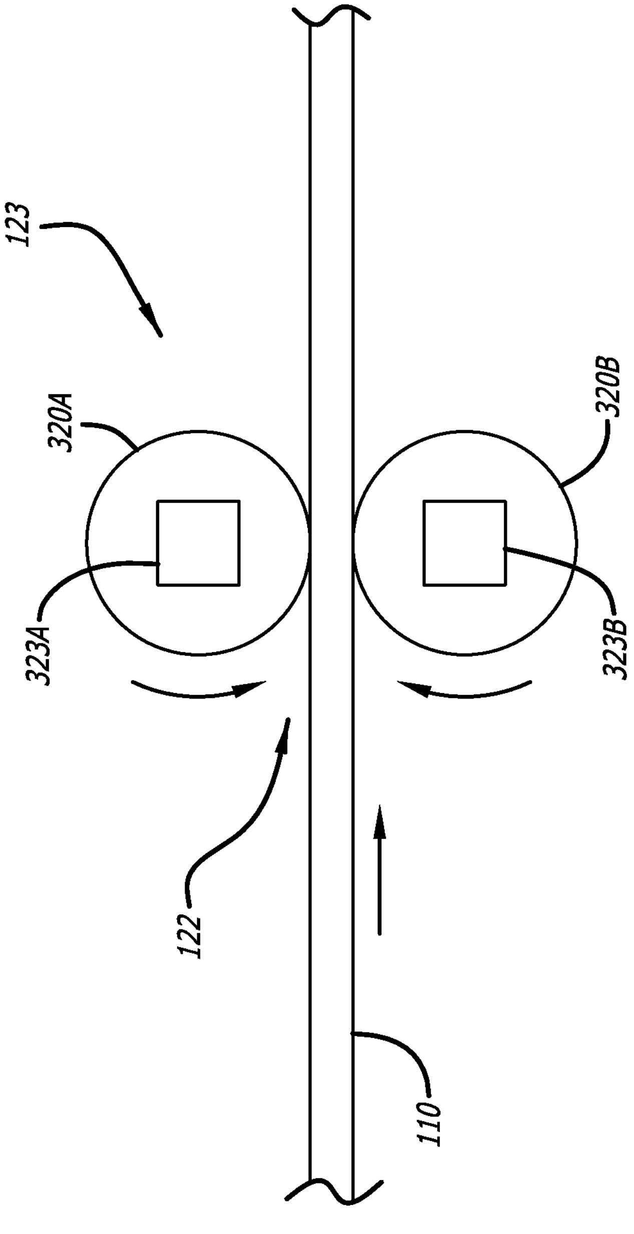
FIG. 3 is detailed illustration of one example of the device engagement mechanism of the system of FIG. 1A, in accordance with some embodiments.

FIG. 3 illustrates one example of the device engagement mechanism 123 of the system 100. In the illustrated example, the device engagement mechanism 123 includes opposing wheels 320A, 320B configured to frictionally engage the medical device 110 between the opposing wheels 320A, 320B. Corresponding engagement actuators 323A, 323B counter rotate the opposing wheels 320A, 320B to longitudinally displace the medical device 110 through/along the active area 122. As may be appreciated by one of ordinary skill, the device engagement mechanism 123, is just one of any number of device engagement mechanism that may be employed to displace the medical device 110 through the active area 122 and, as such, any suitable mechanism for coupling with and displacing the medical device 110 through the active area 122 is included in this disclosure.

Figure 4:
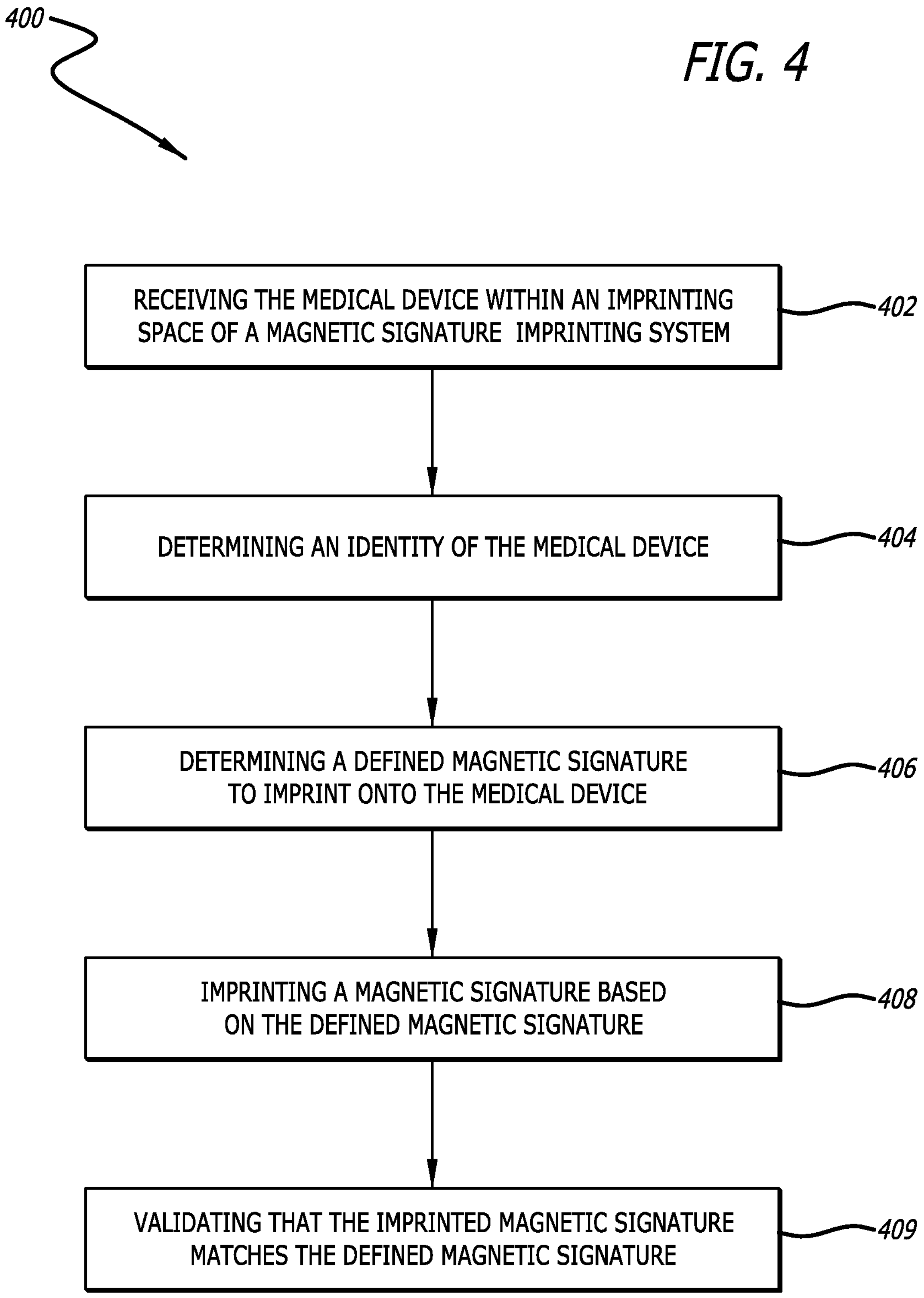
FIG. 4 illustrates a flow chart of an exemplary method of imprinting a magnetic signature onto a medical device, in accordance with some embodiments.

FIG. 4 illustrates a flow chart of an exemplary method 400 of imprinting a magnetic signature onto the medical device 110 that, in accordance with some embodiments, includes all or a subset of the following steps or processes.

The method includes receiving the medical device within the active area (block 402). In some embodiments, embodiments receiving the medical device includes receiving the medical device into the opening of the body. In some embodiments, embodiments receiving the medical device includes receiving the medical device into the imprinting space.

In some embodiments, the method 400 includes determining an identity of the medical device (block 404). Determining the identity may include determining the type of medical device, such as a needle, a stylet, a guidewire, an obturator, a probe, or a tunneller. In some embodiments, determining an identity of the medical device includes detecting and identifying one or more characteristics of the medical device including physical characteristics, such as the size of the medical device, the shape of the medical device, the location of the ferrous elements on the medical device, for example. In some embodiments, determining an identity of the medical device includes obtaining receiving RFID data from a RFID tag associated with the medical device, where the RFID data includes the identity. In some embodiments, determining an identity of the medical device includes obtaining receiving barcode data from a barcode associated with the medical device, where the barcode data includes the identity.

In some embodiments, the method 400 includes defining the magnetic signature to imprint onto the medical device 110 (block 406) or in other words, determining a defined magnetic signature to imprint onto the medical device 110. In some embodiments, the determining the defined magnetic signature to imprint onto the medical device includes determining the magnetic signature based on the determined identity. In some embodiments, determining the defined magnetic signature to imprint onto the medical device includes choosing a magnetic signature from a plurality a magnetic signatures stored in memory where each of the plurality a magnetic signatures is linked to an identity of one of a corresponding plurality of medical devices.

In some embodiments, the method 400 further includes imprinting a magnetic signature onto the medical device (block 408) or in other words, defining an imprinted magnetic signature on the medical device. In some embodiments of the method, imprinting a magnetic signature includes activating the one or more electromagnets of the system, where each electromagnet is configured to imprint a dipole onto the medical device when activated. Activating the one or more electromagnets may also include (i) activating a first pair of electromagnets separated by a first electromagnet spacing, where the first electromagnet spacing defines a first spacing be adjacent dipoles; and (ii) activating a second pair of electromagnets separated by a second electromagnet spacing, where the second electromagnet spacing defining a second spacing be adjacent dipoles, and where second spacing between adjacent dipoles is different from the first spacing between adjacent dipoles. Activating one or more electromagnets may also include (i) activating the first electromagnet to imprint a dipole having a first dipole length and (ii) activating the second electromagnet to imprint a dipole having a second dipole length, wherein the second dipole length is different from the first dipole length. Activating one or more electromagnets may also include (i) supplying power via the power converter to one electromagnet in a first polarity to imprint a first dipole having a first orientation, and (ii) supplying power to the same electromagnet in a second polarity to imprint a second dipole having a second orientation opposite the first orientation. Activating the one or more electromagnets may also include (i) activating a first subset of the electromagnets, (ii) displacing the medical device from a first position within the imprinting space to a second position within the imprinting space, and (iii) activating a second subset of the electromagnets. Imprinting a magnetic signature may also include (i) determining a longitudinal position of at least a portion of the imprinted magnetic signature within the imprinting space via one or more magnetometers of the system, and (ii) displacing the medical device via device engagement mechanism to adjust the longitudinal position of the at least a portion of the imprinted magnetic signature within the imprinting space.

In some embodiments, the method 400 further includes validating that the imprinted magnetic signature matches the defined magnetic signature validating the magnetic signature of the medical device (block 410). In some embodiments of the method, validating the imprinted magnetic signature includes (i) determining the imprinted magnetic signature via the number of magnetometers of the system and (ii) comparing the imprinted magnetic signature with the defined magnetic signature to verify that the imprinted magnetic signature matches the defined magnetic signature.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A magnetic signature imprinting system, comprising:
an imprinting apparatus configured to operatively engage a medical device, the imprinting apparatus comprising:
a frame;
a device engagement mechanism coupled with the frame, the device engagement mechanism configured to receive and position the medical device within an imprinting space of the frame, the medical device including one of a needle, a stylet, a guidewire, an obturator, a probe, a tunneller, a stent, a port, a balloon device, or a sheath; and
a number of electromagnets disposed within the imprinting space; and
a console coupled with the number of electromagnets, the console having a number of processors and a non-transitory computer-readable medium having logic stored thereon that, when executed by the number of processors, performs operations that include selectively activating one or more of the number of electromagnets to imprint a defined magnetic signature on the medical device to define an imprinted magnetic signature that includes a series of dipoles disposed along the medical device.

2. The system according to claim 1, wherein at least one dipole includes a first length and at least one other dipole includes a second length different from the first length.

3. The system according to claim 1, wherein at least one dipole includes a first orientation and at least one other dipole includes a second orientation rotated 180 degrees from the first orientation.

4. The system according to claim 1, wherein a first spacing between a first pair of adjacent dipoles is different from a second spacing between a second pair of adjacent dipoles.

5. The system according to claim 1, wherein the imprinted magnetic signature includes one or more multipoles disposed along the medical device.

6. The system according to claim 1, further comprising a number of identification sensors coupled with the console, the number of identification sensors configured to provide at least one of data or electrical signals associated with one or more characteristics of the medical device, wherein the operations further include:

receiving the at least one of data or electrical signals from the number of identification sensors;

determining an identity of the medical device based on the at least one of data or electrical signals; and establishing the defined magnetic signature based on the identity.

7. The system according to claim 6, wherein:

the number of identification sensors includes a radio frequency identification (RFID) reader; and the operations further include receiving RFID data from an RFID tag associated with the medical device, the RFID data including the identity.

8. The system according to claim 6, wherein:

the number of identification sensors includes a barcode reader; and the operations further include obtaining barcode data from a barcode associated with the medical device, the barcode data including the identity.

9. The system according to claim 6, wherein:

the number of identification sensors includes one or more first sensors configured to provide the at least one of data or electrical signals based on a number of physical characteristics of the medical device; and the operations further include determining the identity based on the number of physical characteristics.

10. The system according to claim 9, wherein the number of physical characteristics include one or more of a physical dimension or a shape of the medical device.

11. The system according to claim 10, wherein the physical dimension includes at least one of a length or a diameter of the medical device.

12. The system according to claim 9, wherein the one or more first sensors include at least one of an inductive sensor, an impedance sensor, a capacitive sensor, or an optical sensor.

13. The system according to claim 1, further comprising a number of magnetometers coupled with the console, the number of magnetometers configured to detect a magnetic field generated by the imprinted magnetic signature on the medical device, wherein the operations further include:

receiving electrical signals from the number of magnetometers based on the magnetic field generated by the imprinted magnetic signature;

determining the imprinted magnetic signature on the medical device from the electrical signals from the number of magnetometers;

comparing the imprinted magnetic signature with the defined magnetic signature to verify that the imprinted magnetic signature matches the defined magnetic signature; and providing an alert to an operator in response to the comparing of the imprinted magnetic signature with the defined magnetic signature.

14. The system according to claim 1, wherein:

activating one or more of the number of electromagnets includes activating a pair of electromagnets that are separated by an electromagnet spacing; and the electromagnet spacing defines a spacing between adjacent dipoles of the imprinted magnetic signature.

15. The system according to claim 1, wherein:

activating one or more of the number of electromagnets includes:

activating a first pair of electromagnets separated by a first electromagnet spacing, the first electromagnet spacing defining a first spacing between adjacent dipoles; and activating a second pair of electromagnets separated by a second electromagnet spacing, the second electromagnet spacing defining a second spacing between adjacent dipoles, the second spacing between adjacent dipoles being different from the first spacing between adjacent dipoles.

16. The system according to claim 1, wherein:

the number of electromagnets includes a first electromagnet having a first electromagnet length and second electromagnet having a second electromagnet length different from the first electromagnet length, and activating one or more of the number of electromagnets includes:

activating the first electromagnet to imprint a first dipole having a first dipole length; and activating the second electromagnet to imprint a second dipole having a second dipole length, wherein the second dipole length is different from the first dipole length.

17. The system according to claim 1, wherein:

the console includes a power converter configured to supply power to the number of electromagnets in a first polarity and in a second polarity opposite the first polarity, and activating one or more of the number of electromagnets includes:

supplying power to one electromagnet in the first polarity to imprint a first dipole having a first orientation; and supplying power to the one electromagnet in the second polarity to imprint a second dipole having a second orientation opposite the first orientation.

18. The system according to claim 1, wherein:

the device engagement mechanism is configured to displace the medical device along the imprinting space, and activating one or more of the number of electromagnets includes:

activating a first subset of electromagnets;

displacing the medical device from a first position within the imprinting space to a second position within the imprinting space; and activating a second subset of electromagnets.

19. The system according to claim 18, wherein:

the imprinting apparatus includes a number of position sensors configured to determine a longitudinal position of the medical device within the imprinting space, and the operations further include at least one of notifying an operator regarding the longitudinal position of the medical device or adjusting a position of the medical device via the device engagement mechanism.

20. The system according to claim 19, wherein:

the number of position sensors includes one more magnetometers configured to determine a longitudinal position of at least a portion of the imprinted magnetic signature within the imprinting space, and the operations further include adjusting the position of the medical device via the device engagement mechanism to move the at least a portion of the imprinted magnetic signature from the first position within the imprinting space to the second position within the imprinting space.

* * * * *